US007939056B2

(12) United States Patent
Horwitz et al.

(10) Patent No.: US 7,939,056 B2
(45) Date of Patent: May 10, 2011

(54) INTERLEUKIN-10 COMPOSITIONS FOR THE TREATMENT OF ADENOCARCINOMAS

(75) Inventors: Bruce Horwitz, Lexington, MA (US); James Fox, Harvard, MA (US); Susan Erdman, Hopkinton, MA (US); Anne Davidson, Ardsley, NY (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 532 days.

(21) Appl. No.: 11/598,002

(22) Filed: Nov. 13, 2006

(65) Prior Publication Data

US 2007/0122383 A1     May 31, 2007

Related U.S. Application Data

(60) Provisional application No. 60/735,856, filed on Nov. 14, 2005.

(51) Int. Cl.
*A61K 38/19*     (2006.01)
*A61K 38/20*     (2006.01)
*C12N 15/00*     (2006.01)

(52) U.S. Cl. ............... 424/85.1; 514/21.2; 514/19.3; 514/10.3; 435/69.7

(58) Field of Classification Search .................. None
See application file for complete search history.

(56) References Cited

U.S. PATENT DOCUMENTS

| 5,368,854 | A | 11/1994 | Rennick |
| 6,403,077 | B1 | 6/2002 | Strom et al. |
| 6,410,008 | B1 | 6/2002 | Strom et al. |
| 2002/0173628 | A1 | 11/2002 | Strom et al. |
| 2003/0026778 | A1 * | 2/2003 | Strom et al. ............... 424/85.2 |
| 2003/0109690 | A1 * | 6/2003 | Ruben et al. ............... 536/23.1 |

FOREIGN PATENT DOCUMENTS

WO     WO 02/077033     * 10/2002

OTHER PUBLICATIONS

Kim et al., Oncogene, Mar. 11, 2004, vol. 23(10):1838-1844.*
Berman et al., J. Immunol., 1996, vol. 157:231-238.*
Khosravi-Far et al., cancer Metastasis Rev., 1994, vol. 13(1):67-89.*
Colombel, et al., "Interleukin 10 (Tenovil) in the Prevention of Postoperative Recurrence of Crohn's Disease," *Gut* 49:42-46 (2001).
Erdman, et al., "CD4+ CD25+ Regulatory T Lymphocytes Inhibit Microbially Induced Colon Cancer in Rag2-Deficient Mice," *Am. J. Pathol.* 162:691-702 (Feb. 2003).
Erdman, et al., CD4+ CD25+ Regulatory Lymphocytes Require Interleukin 10 to Interrupt Colon Carcinogens in Mice[1], *Cancer Res.* 63:6042-6050 (Sep. 2003).
Erdman, et al., CD4+ CD25+ Regulatory Lymphocytes Induce Regression of Intestinal Tumors in $Apc^{Min/+}$ Mice, *Cancer Res.* 65:3998-4004 (May 2005).
Fedorak, et al., "Recombinant Human Interluekin 10 in the Treatment of Patients With Mild to Moderately Active Crohn's Disease," *Gastroenterology* 119:1473-1482 (2000).

Fiorentino, et al., "Two Types of Mouse T Helper Cell IV," *J. Exp. Med.* 170:2081-2089 (Dec. 1989).
Fiorentino, et al., "IL-10 Inhibits Cytokine Production by Activated Macrophages[1]," *J. Immunol.* 147:3815-3822 (Dec. 1991).
Flores-Villanueva, et al., "Recombinant IL-10 and IL10/Fc Treatment Down-Regulate Egg Antigen-Specific Delayed Hypersensitivity Reactions and Egg Granuloma Formation in Schistosomiasis," *J. Immunol.* 156:3315-3320 (1996).
Gerard, et al., "Interleukin 10 Reduces the Release of Tumor Necrosis Factor and Prevents Lethality in Experimental Endotoxemia," *J. Exp. Med.* 177:547-550 (Feb. 1993).
Kim, et al., "Synergism of Cytoplasmic Kinases in IL6-Induced Ligand-Independent Activation of Androgen Receptor in Prostate Cancer Cells," *Oncogene* 23:1838-1844 (2004).
Li, et al., "IL-10 and It's Related Cytokines for Treatment of Inflammatory Bowel Disease," *World J. Gastroenterol.* 10(5):620-625 (2004).
Maloy, et al., "CD4+CD25+ $T_R$ Cells Suppress Innate Immune Pathology Through Cytokine-Dependent Mechanisms," *J. Exp. Med.* 197:111-119 (Jan. 2003).
Mihara, et al., "CTLA4Ig Inhibits T-Cell Dependent B-Cell Maturation in Murine Systemic Lupus Erythematosus," *J. Clin. Invest.* 106:91-101 (Jul. 2000).
Moore, et al., "Interleukin-10 and the Interleukin-10 Receptor," *Annu. Rev. Immunol.* 19:683-765 (2001).
Moore, et al., "Homology of Cytokine Synthesis Inhibitory Factor (IL-10) to the Epstein-Barr Virus Gene BCRFI," *Science* 248:1230-1234 (Jun. 1990).
O'Garra, et al., "Production of Cytokines by Mouse B Cells: B Lymphomas and Normal B Cells Produce Interleukin 10," *Internat. Immunol.* 2:821-832 (1990).
Powrie, et al., "T Cells in Inflammatory Bowel Disease: Protective and Pathogenic Roles," *Immunity* 3:171-174 (Aug. 1995).
Powrie, et al., "Regulating the Regulators," *Science* 299:1030-1031 (Feb. 2003).
Schreiber, et al., "Safety and Efficacy of Recombinant Human Interleukin 10 in Chronic Active Crohn's Disease," *Gastroenterology* 119:1461-1472 (2000).
Van Deventer, et al., "Multiple Doses of Intravenous Interleukin 10 in Steroid-Refractory Crohn's Disease," *Gastroenterology* 113:383-389 (1997).
Viera, et al., "Isolation and Expression of Human Cytokine Synthesis Inhibitory Factor cDNA clones: Homology to Epstein-Barr Virus Open Reading Frame BCRF1," *Proc. Natl. Acad. Sci. USA* 88:1172-1176 (Feb. 1991).

(Continued)

*Primary Examiner* — Elizabeth C. Kemmerer
*Assistant Examiner* — Xiaozhen Xie
(74) *Attorney, Agent, or Firm* — Law Office of: Michael A. Sanzo, LLC

(57) ABSTRACT

The present invention is directed to methods for the treatment of adenocarcinomas that are characterized by the overexpression of a particular oncogene, Pim-1. The procedure involves administering a therapeutically effective amount of interleukin-10 that has been coupled to a carrier that increases its circulating plasma half-life.

20 Claims, No Drawings

OTHER PUBLICATIONS

Zheng, et al., "A Noncytolytic IL-10/Fc Fusion Protein Prevents Diabetes, Blocks Autoimmunity, and Promotes Suppressor Phenomena in NOD Mice[1]," *J. Immunol.* 158:4507-4513 (1997).

Zheng, et al., "Administration of Noncytolytic IL-10/Fc in Murine Models of Lipopolysaccharied-Induced Septic Shock and Allogeneic Islet Transplantation[1]," *J. Immunol.* 154:5590-5600 (1995).

International Preliminary Report on Patentability for PCT/US06/43900 filed Nov. 13, 2006.

International Search Report for PCT/US06/43900 filed Nov. 13, 2006.

Written Opinion of the International Searching Authority for PCT/US06/43900 filed Nov. 13, 2006.

* cited by examiner

INTERLEUKIN-10 COMPOSITIONS FOR THE TREATMENT OF ADENOCARCINOMAS

CROSS REFERENCE TO RELATED APPLICATIONS

The present application claims priority to, and the benefit of, U.S. provisional application 60/735,856, filed on Nov. 14, 2005, the contents of which is hereby incorporated by reference in its entirety.

STATEMENT OF GOVERNMENT FUNDING

The United States Government has a paid-up license in this invention and the right in limited circumstances to require the patent owners to license others under reasonable terms as provided for by the terms of NIH Grant Nos. R01AI052267-02; R01CA67529; and R01AI50952, awarded by the Department of Health and Human Services.

FIELD OF THE INVENTION

The present invention is directed to treatment methods for adenocarcinomas that are characterized by the overexpression of the Pim-1 oncogene. The method involves administering a therapeutically effective amount of a compound comprising interleuken-10 (IL10) joined to an inactive carrier that increases its circulating plasma half-life by a factor of at least 2.

BACKGROUND OF THE INVENTION

Interleukin 10 (IL-10) is a cytokine produced by T lymphocytes, B lymphocytes and macrophages that was first identified based on its ability to inhibit interferon gamma and IL-2 synthesis (Fiorentino, et al., *J. Exp. Med.* 170:2081-2089 (1989); Moore, et al., *Science* 248:1230-1252 (1990); Vieira, et al., *Proc. Nat'l Acad. Sci. USA* 88:1172-1177 (1991); O'Garra, et al., *Internat. Immunol.* 2:821-828 (1990); Fiorentino, et al., *J. Immunol.* 147:3815-3822 (1991)). IL10 has since been shown to have a variety of biological functions and has been extensively studied for possible therapeutic use in connection with inflammatory bowel disease and autoimmune diseases such as psoriasis, rheumatoid arthritis, and multiple sclerosis (Li, et al., *World J. Gastroenterol.* 10(5): 620-625 (2004)).

IL10 has also received attention as a potential treatment for cancers in which inflammation is known to be a predisposing factor, particularly cancers of the colon. 129/SvEv Rag2$^{-/-}$ mice, which lack mature lymphocytes, have been shown to develop colitis and colon cancer following infection with a widespread enteric bacterial mouse pathogen *Helicobacter hepaticus* (Erdman, et al., *Am. J. Pathol.* 162:691-702 (2003); Erdman, et al., *Cancer Res.* 63:6042-6050 (2003)). The inflammatory bowel disease and carcinoma that develop in *H. hepaticus*-infected Rag2$^{-/-}$ mice are abrogated by treatment with IL10-competent regulatory cells (Erdman, et al., *Cancer Res.* 63:6042-6050 (2003)). Other studies using immunedeficient mice have revealed similar protective and therapeutic effects mediated by CD4$^+$ regulatory cells in mice with colitis (Powrie, *Immunity* 3:171-174 (1995); Maloy, et al., *J. Ex. Med.* 197:111-119 (2003)). Interestingly, adoptive transfer of regulatory cells lacking IL10 is not protective, but instead exacerbates the malignant phenotype such that 100% of male recipients rapidly develop mucinous colonic tumors that invaded the peritoneal cavity (Erdman, et al., *Cancer Res.* 63:6042-6050 (2003)).

The development of IL10 as a therapeutic has been limited, in part, by its short plasma half life. In this regard, it has been suggested that IL10 is only effective for about 30 minutes following administration and attempts have been made to increase its duration of action by coupling it to other proteins with longer half lives (Gerard, et al., *J. Exp. Med.* 177:547 (1993); U.S. Pat. No. 6,410,008; U.S. Pat. No. 6,403,077). Other problems are that there has not been any reliable method of predicting which types of tumors, if any, IL10 is likely to be effective against and its complex biological effects make the routine administration of very large doses of IL10 undesirable.

SUMMARY OF THE INVENTION

The present invention is based upon experiments indicating that certain forms of IL10 are effective in treating adenocarcinomas in cases where tumors are characterized by the overexpression of a particular oncogene, Pim-1. The method should be effective against such adenocarcinomas regardless of their tissue of origin and regardless of whether there has been a prior inflammatory condition. The results obtained suggest that IL10 is probably exerting its therapeutic effects by suppressing IL6. This suggests that other inhibitors of IL6 should also be effective against adenocarcinomas overexpressing Pim-1, especially in cases where IL6 is also overexpressed.

In its first aspect, the invention is directed to a method of treating a patient for an adenocarcinoma which overexpresses Pim-1 by administering a therapeutic compound comprising human IL10 joined to a carrier. The carrier can be any nontoxic, pharmaceutically acceptable molecule that is capable of being coupled to IL10 and which, after coupling, increases the circulating plasma half-life of IL10 by a factor of at least 2. Enzymatically inactive proteins are one type of carrier that can be used, with the Fc region of a human IgG (especially IgG2a) being preferred. The therapeutic compound should have a circulating half-life of at least four hours with a half-life of at least eight hours being preferable.

Therapeutic compounds used in the method described above may either be conjugates, i.e., compounds in which IL10 is chemically joined to carrier (optionally, with a spacer between the two) or chimeras, i.e., a recombinantly produced fusion proteins in which IL10 is joined by a peptide bond to a carrier protein (again, optionally separated by a spacer). The therapeutic compounds will typically be part of a pharmaceutical composition containing a fluid in which they are dissolved, suspended or emulsified, and one or more excipients. The most preferred route of administration is by injection or infusion at a dose of between 0.5 μg/kg body weigh and 50 μg/kg body weight (the final dose typically being 0.5-5 mg).

The method will be particularly effective in treating adenocarcinomas of the colon, breast or prostate since tumors in these locations are often associated with elevated Pim-1 levels. As long as the tumor overexpresses this oncogene, it will not matter whether it has arisen subsequent to a prior inflammatory condition or not. For example, the treatment should be effective against colon cancers regardless of whether a patient has previously experienced an inflammatory bowel disease.

In a more specific aspect, the invention is directed to a method of treating a patient for an adenocarcinoma overexpressing the Pim-1 oncogene by administering an effective amount of a chimeric protein in which IL10 is fused to the Fc region of a human immunoglobulin (Ig, preferably human IgG2a). The chimeric protein should have a circulating plasma half-life at least twice as long as free IL10, i.e., IL10 not joined to a carrier. It is also preferred that the chimeric protein include the hinge region of the Ig and that the IL10 be fused to this region. The Fc region of IgG can be chemically synthesized or be produced by digesting a purified IgG with papain using standard biochemical methods. The Fc region is preferably non-lytic, i.e., modified so that it lacks a high affinity Fc receptor binding site and a C'1q binding site. However, lytic forms of Fc, e.g., the unmodified protein, may also be coupled to an Ig and used. As with the methods described above, the circulating half-life of the chimera should preferably be at least four hours, and it should preferably be administered by injection or infusion at a dose of between 0.5 and 50 µg/kg body weight. The most preferred adenocarcinomas for treatment will be those of the prostate, breast and colon regardless of whether these cancers arise subsequent to an inflammatory condition or not.

In another aspect, the invention is directed to a method of treating a patient for an adenocarcinoma in which a biological sample from the patient, i.e., a sample of tumor tissue, is assayed to determine if it is producing more Pim-1 oncogene than the amount present in normal tissue of the same type of organ. Pim-1 levels may be determined either using a PCR assay (e.g., of the type described in Cancer Res. 63:8079-8084 (2003)) or by means of an ELISA assay (e.g., of the type commercially available from Perbio Science, a division of Fischer Biosciences, Lausanne, Switzerland). If the results of the assay for Pim-1 indicate that the adenocarcinoma is producing a greater than normal amount of this oncogene, then the patient is treated with a pharmaceutical composition containing an effective amount of IL10 joined to a carrier that increases its circulating plasma half-life. Any of the forms of IL10 described herein may be used for this purpose with chimeras that include the Fc region of a human IgG being preferred. Again, dosages should generally be in the range of 0.5-50 µg/kg body weight, with the method being particularly effective against cancer of the breast, prostate or colon.

Finally, the invention includes therapeutic packages containing a pharmaceutical composition of the type described herein, i.e., containing as an active agent IL10 joined to a carrier that increases its circulating plasma half-life by a factor of at least 2. The pharmaceutical composition should be in a finished injection ampoule, vial or syringe and the package should contain instructions for the administration of the pharmaceutical composition to a patient for the treatment of an adenocarcinoma, particularly adenocarcinomas of the breast, prostate or colon that overexpress Pim-1. In a preferred embodiment, the therapeutic package also includes components necessary to perform an assay to determine Pim-1 levels in a biological sample. Most typically, these components will include either antibodies directed against the Pim-1 gene product or PCR primers that can be used to amplify nucleic acids corresponding to Pim-1.

DEFINITIONS

The following definitions are provided for the purpose of comprehension of the present invention but are not meant to be limiting.

Adenocarcinoma: A cancer that starts in the glandular epithelial cells of internal organs, particularly colorectal cancers or cancers of the breast or prostate.

Interleukin 10 (IL10): Any form of IL10 known in the art could be used in the compositions described herein. For experimental work, the mouse form of IL10 is particularly useful. This has been fully described and sequenced (see Moore et al., Science 248:1230-1234 (1990); and U.S. Pat. No. 5,231,012). However, the most preferred form of IL10 for clinical use is the human form which has also been fully described and its sequence provided in numerous places including U.S. Pat. No. 5,231,012. Sequences also appear in U.S. Pat. No. 6,018,036 and U.S. Pat. No. 6,319,493. Those of skill in the art will recognize that some of the amino acid residues in IL10 may be changed without affecting its activity and that these modified forms of IL10 could also be joined to a carrier and used in the methods described herein.

Patient or Subject: Although the present compositions and methods are intended primarily for use in humans, they may also be effectively employed for both domestic animals (cats or dogs) and farm animals (cattle, sheep, horses, pigs etc). Thus, it will be understood that the terms "patient" and "subject" include these other animals unless context indicates otherwise.

Conjugates: As used herein, the term "conjugate" refers to a compound in which IL10 has been chemically joined to a carrier. This joining may be either covalent, e.g., by chemical coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. Conjugates differ from chimeric proteins with respect to the way that they are made.

Chimera: A "chimera" or "chimeric protein," as these terms are used herein, refers to the recombinant product produced when a nucleotide sequence encoding IL10 is coupled to a nucleotide sequence for a carrier protein, and this sequence is then used to make a fusion protein. The Examples section herein describes such a chimera.

Carrier: The carrier joined to IL10 as described herein is any, nontoxic pharmaceutically acceptable molecule that can be coupled to IL10 and increase its circulating plasma half life by a factor of at least 2 and preferably by a factor of at least 10. Preferably the carrier is an enzymatically inactive protein with the most preferred being a non-lytic human IgG Fc protein.

Effective Amount or Therapeutically Effective Amount: As used herein, these terms refer to an amount of a composition sufficient to achieve a desired biological effect. For example, depending on the context, an effective amount may be an amount of IL10 conjugate sufficient to shrink a tumor of the colon or to slow its growth.

Isolated: The term "isolated" refers to a molecule that has been removed from its native environment. For example, a protein in a living animal is not "isolated," but the same protein separated from the materials of its natural state, e.g., purified by some biochemical procedure, is "isolated."

Purified: When the term "purified" is used in reference to a molecule, it means that the concentration of the molecule has been increased relative to molecules associated with it in its natural environment, or the environment in which it was produced, found or synthesized. Naturally associated molecules include proteins, nucleic acids, lipids and sugars but generally do not include water, buffers, and reagents added to maintain the integrity or facilitate the purification of the molecule being purified. According to this definition, a substance may be at least 20%, 40%, 60%, 80%, 90%, 95% or 99% pure when considered relative to its contaminants.

Fc region of an IgG: The IgG C-terminal domain that is produced by digesting IgG with papain. IgG Fc has a molecular weight of approximately 50 kD. In the molecules of the invention, the entire Fc region can be used, or only a half-life enhancing portion. In addition, many modifications in amino acid sequence are acceptable, as native activity is not in all cases necessary or desired.

Non-lytic IgG Fc: An IgG Fc region which lacks a high affinity Fc receptor binding site and which lacks a C'1q binding site. Methods for appropriately modifying the Fc region are taught in U.S. Pat. No. 6,403,077 and in published U.S. application 2004/0228856.

Lytic IgG Fc: An IgG Fc region which has a high affinity Fc receptor binding site and a C'1q binding site. The native, unmodified form of the protein would be lytic. Lytic IgG Fc can target cells for antibody dependent cellular cytotoxicity (ADCC) or complement directed cytolysis (CDC).

IgG hinge region: The portion of a naturally-occurring IgG which includes the cysteine residues at which disulfide bonds link the two heavy chains of the immunoglobulin. For IgG1, the hinge region also includes the cysteine residues at which the disulfide bonds linking the .gamma.1 and light chains form. The hinge region is approximately 13-18 amino acids in length in IgG1, IgG2, and IGg4; in IgG3, the hinge region is approximately 65 amino acids in length.

Spacer: A spacer may be included between the carrier and IL10, in conjugates or chimeras to separate the two. A spacer may take the form, for example, of an unbranched amino acid chain 1-100, preferably 2-20, residues in length.

DETAILED DESCRIPTION OF THE INVENTION

Making of Conjugates

It will be understood that the term "conjugates" as used herein refers compounds in which IL10 and carrier are joined, regardless of how the linking is accomplished. For example standard chemical methods may be used to synthesize a conjugate in which IL10 and carrier are joined at a specific position. An alternative procedure is to separately obtain the IL10 and carrier and then join them together. For example, a protein with IL10 activity may be synthesized with an amino acid position (the one where carrier is to attach) occupied by a reactive group and all other possible attachment sites occupied by blocking groups. The carrier may then be synthesized with a complementary reactive group to facilitate attachment. After the IL10 and carrier are joined, the blocking groups may be removed using standard methodology.

Many methods for chemically joining a protein to another compound have been described in the art and may be adapted to the conjugation of IL10 (see e.g., Sambrook, et al., eds., *Molecular Cloning A Laboratory Manual,* 2nd. edition, Cold Spring Harbor Laboratory Press, Cold Spring Harbor, N.Y. (1989); Ausubel, et al., eds., *Current Protocols in Molecular Biology*, John H. Wiley & Sons, Inc. (1997); Celis, ed., *Cell Biology* Academic Press, 2$^{nd}$ edition, (1998)), all of which are incorporated herein by reference in their entireties.)

Methods of attachment may involve the use of heterobifunctional cross-linkers. These include the cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available, for example from the Pierce Chemical Company (Rockford, Ill., USA), and having one functional group reactive towards amino groups and one functional group reactive towards SH residues. The above mentioned cross-linkers all lead to formation of a thioether linkage. Another class of cross-linkers that might be used the practice of the invention is characterized by the introduction of a disulfide linkage between the linked components. Cross-linkers belonging to this class include for example SPDP and Sulfo-LC-SPDP (Pierce).

Proteins may also be coupled by cross-linking using carbodiimide compounds. These include the carbodiimide EDC (1-(3-dimethylaminopropyl)-3-ethylcarbodiimide hydrochloride), which can optionally also be used with N-hydroxysuccinimide NHS in the reaction. Additional cross-linking methods and cross-linkers, suitable for attaching antigens as well as guidance on performing the coupling reactions and on the use of chemical cross-linkers can be found in Hermanson, *Bioconjugate Techniques*, Academic Press Inc., San Diego, Calif., USA.

Other methods of forming conjugates may involve biotinylating one component, i.e., either IL10 or carrier, and linking the other component to avidin or streptavidin. Many variations of this procedure may be used as will be readily apparent to those of skill in the art. For example, both components may be biotinylated and then coupled with a streptavidin or avidin linker.

Preparation of Chimeras

Methods for making IL10/carrier chimeras utilize standard techniques of molecular biology (see e.g., Sambrook, et al., eds., *Molecular Cloning A Laboratory Manual,* 2nd. edition, Cold Spring Harbor Laboratory Press, Cold Spring Harbor, N.Y. (1989); Ausubel, et al., eds., *Current Protocols in Molecular Biology*, John H. Wiley & Sons, Inc. (1997); Celis, ed., *Cell Biology* Academic Press, $2^{nd}$ edition, (1998)). Specific methods are fully described in U.S. Pat. No. 6,410,008 and can be directly adopted for use in connection with the present invention.

The following is an example of a procedure that can be used to make a chimera suitable to use in connection with the methods described herein. The example is written in terms of mouse IL10 (mIL10) but the methods could be used in essentially the same way for the human cytokine.

Full length mIL-10 (1-178) is cloned by RT-PCR from mouse spleen cells using a 5' primer homologous to the 5' mIL-10 leader with the addition of a Hind III restriction site and a 3' primer consisting of the last 23 bp of mIL10 and the first 20 bp of the mouse IgG2a CH2 region (5' ACA TGA CAA TTA AAG CCA GGC TGG AGC CCA GAG GGC CCA CAA T 3' (SEQ ID NO: 1)). The reverse of the 3' primer is used together with the appropriate 3' primer (5' TTT CTA GAT CAT TTA CCC GGA GT 3' (SEQ ID NO:2)) containing an XbaI site to PCR amplify the mouse IgG2a segment. This Ig segment had been previously mutated so that it no longer binds to the Fc Receptor. The two PCR fragments thus generated are purified using Geneclean (Bio 101, Vista Calif.), then mixed together in a 1:1 molar ratio and annealed by heating to 94° C. and slowly cooling to 37° C. The annealed products are then extended for 7 minutes at 72° C. to generate full length templates for the subsequent PCR reaction. A further 30 rounds of PCR is then performed using the external 5' and 3' primers to generate a full length product containing a HindIII restriction site at the 5' end and a XbaI site at the 3' end. The full length mIL10-IgG is then cloned into a TA vector, sequenced and then subcloned into the HindIII-XbaI site of the pcDNA vector containing the CMV promoter. This plasmid is subjected to partial digestion with EcoRI and the fragment containing the CMV promoter and IL10-IgG is subcloned into the adenovirus shuttle vector pΔE1sp1A (Microbix Systems Toronto Ontario Canada. The shuttle vector is then cotransfected into 293 cells with pBHG10 adenoviral vector and a virus generated as previously described (Reddy, et al., *Transplantation* 71:801 (2001)).

Preferably, the carrier used in the production of the chimeric protein has, by itself, an in vivo circulating half-life at least twice as long as that of IL-10. The circulating half-life of IL-10 can be measured in by ELISA assay of serum samples. In such ELISAs, antibodies directed against IL-10 can be used as the capture antibody, and antibodies directed against the enzymatically inactive protein can be used as the detection antibody. Such an ELISA can allow for the detection of only the chimeric IL-10 protein in a sample. A working example of such an ELISA is provided in U.S. Pat. No. 6,410,008.

Numerous polypeptides are suitable for use as an enzymatically inactive carrier protein in the invention. Preferably, the protein has a molecular weight of at least 10 kD; a net neutral charge at pH 6.8; a globular tertiary structure; human origin; and no ability to bind to surface receptors other than the IL-10 receptor. Where the enzymatically inactive protein is IgG, preferably, the IgG portion is glycosylated.

The carrier used in the invention is preferably the Fc region of a human IgG molecule and lacks a variable region of the IgG heavy chain. A person skilled in molecular biology can readily produce such molecules from an IgG2a-secreting hybridoma (e.g., HB129) or other eukaryotic cells or baculovirus systems. If desired, the Fc region can be mutated to inhibit its ability to fix complement and bind the Fc receptor (see, U.S. Pat. Nos. 6,410,008 and 2004/0228856). Other useful enzymatically inactive proteins include human serum albumin, transferrin, enzymes such as t-PA which have been inactivated by mutations, and other proteins with a long circulating half-life.

The chimeric protein can be synthesized (e.g., in mammalian cells) using standard methods of recombinant protein expression. If desired, the chimeric protein can be affinity purified according to standard protocols with antibodies directed against IL-10. Antibodies directed against the enzymatically inactive protein are also useful for purifying the chimeric protein by standard immunoaffinity techniques.

Pharmaceutical Compositions and Their Use

The IL10 conjugates and chimeras described herein will typically be administered to a patient as part of a pharmaceutical composition. In addition to the active agents, such a composition may include salts, buffers, and other substances, or excipients which may be desirable for improving its efficacy. Examples of suitable components as well as general guidance with regard to methods for preparing effective compositions may be found in standard texts such as Remington's Pharmaceutical Sciences (Osol, A, ed., Mack Publishing Co., (1990)). In all cases, conjugates or chimeras should be present in a "therapeutically effective amount" (i.e., an amount that produces the desired physiological effect) and other components of the composition should be physiologically acceptable.

The pharmaceutical compositions described herein can be administered by either single or multiple dosages of an effective amount of compound. Effective amounts of the compositions of the invention can be determined for a given patient using methods that are standard in the art of pharmacology and clinical medicine. Typically, it is expected that an effective dose based upon the weight of the conjugate or chimera will vary from 0.1 µg/kg body weight to 100 µg/kg body weight, and preferably from 0.5 µg/kg body weight to 50 µg/kg body weight. Typical dosages would be, for example, 0.1-20 mg of compound (typically 0.5-5 mg) dissolved in 1 ml of injectable fluid. Although, the conjugates and chimeras are effective in treating adenocarcinomas overexpressing PIM-1, it is expected that other types of tumors will also be responsive. Thus, as a generalized strategy, the chimeras or conjugates may be administered to any cancer patient to determine whether there is a positive response. Patients treated in this manner may include those with cancers of the colon, breast, prostate, lung, liver, stomach, pancreas, uterus, ovary, brain, kidneys, esophagus, skin etc. Also, other conditions responding to IL-10 may be more effectively treated using the conjugates and chimeras described herein.

Pharmaceutical compositions may be administered to patients by any route known in the art, including injection, inhalation, or by oral administration. However, in order to prevent degradation in stomach acid the preferred method will usually be by intramuscular, intravenous, or subcutaneous injection, by infusion or by implantation of a dosage form that slowly releases composition over a period of time. Suitable carriers that may be used in preparations for injection include sterile aqueous (e.g., physiological saline) or non-aqueous solutions and suspensions such as propylene glycol, polyethylene glycol, vegetable oils such as olive oil, and injectable organic esters such as ethyl oleate. Treatment and dosing strategies may be developed using guidance provided by standard reference works.

Therapeutic Packages

The invention also includes therapeutic packages for use in treating patients. A therapeutic package will comprise at least one container containing the conjugates or chimeras described above along with instructions for administering the compositions to a patient with an adenocarcinoma. Packages may also include components needed to measure either IL6 levels or levels of Pim-1 oncogene, e.g., they may include buffers and primers necessary for a PCR assay or a complete ELISA kit may be present. ELISA kits that are already on the market may be used for this purpose or new antibodies and reagents may be developed using standard methodology. The conjugates or chimeras, along with other components may either be ready for immediate administration or they may be in a lyophilized or concentrated state, requiring reconstitution or dilution before use. In a preferred embodiment the compounds will be used for injection and will be in a finished pharmaceutical container such as an injection ampoule or vial. Alternatively, pharmaceutical compositions may be supplied in prefilled disposable syringes, each containing an amount of compound suitable for administration to a single patient.

Advantages

One of the main advantages of the present invention is that it ties a particular treatment method, the administration of an IL10 conjugate or chimera with a particular type of cancer that it should be effect against, an adenocarcinoma characterized by the overexpression of the Pim-1 oncogene. Thus, by assaying tumor tissue, either directly or indirectly, for this oncogene, a prediction can be made as to whether the IL10 compounds are likely to be effective or whether some other procedure would have a better chance of success. Physicians may therefore want to test adenocarcinomas for levels of Pim-1 and/or IL6. In cases where a high percentage of a certain type of adenocarcinoma, e.g., adenocarcinomas of the breast, are characterized by Pim-1 overexpression, treatment with IL10 conjugates or chimeras may be initiated even in the absence of a Pim-1 or IL6 assay.

Examples

The present example demonstrates that IL10 regulates the expression of a known oncogene, Pim-1, probably through repression of another cytokine, IL6. Results suggest that a signaling pathway comprised, at least in part, of these molecules is crucial for maintaining epithelial homeostasis in the presence of chronic inflammation.

A. Materials and Methods

129/SvEv Rag2-Deficient Mice

All animals were housed in AAALAC approved facilities in static microisolator cages as previously described (Erdman, et al., *Am. J. Pathol.* 162:691-702 (2003)). 129/SvEv Rag2-deficient mice (obtained from Taconic Farms, Germantown, N.Y.) and Tgfβ1-deficient Rag2-deficient mice (obtained from the Mouse Models of Human Cancer Consortium repository, Frederick, Md.) were bred in-house to provide animals for these experiments. Experimental mice dosed with *H. hepaticus* were housed separately in a biocontainment area within the same animal facility.

Experimental Design

Eight-week-old Rag2$^{-/-}$ mice or TGFβ1$^{-/-}$ Rag2$^{-/-}$ mice were subdivided into groups. Rag2$^{-/-}$ recipients of IL10-deficient CD4$^+$CD45RB$^{lo}$CD25$^+$ cells underwent adoptive transfer 48-72 hours prior to *H. hepaticus* infection (Erdman, et al., *Am. J. Pathol.* 162:691-702 (2003); Erdman, et al., *Cancer Res.* 63:6042-6050 (2003)). All of the adoptive transfer recipients in this study were male, based on the earlier observation that microbially-induced cancer was exacerbated in male mice. *H. hepaticus*-infected recipients of IL10-deficient lymphocytes were treated with competent regulatory cells (n=10), IL10-Ig (n=10), or rat anti-mouse IL6 (n=8) at 6 weeks after *H hepaticus* infection, when >90% of males had invasive colonic carcinoma. Replicate experiments were conducted with two or three groups of 4-6 mice each.

Experimental Infection

*H. hepaticus* (strain 3B1, ATCC #51449) was grown under microaerobic conditions, prepared, and confirmed pure as described elsewhere (Erdman, et al., *Am. J. Pathol.* 162:691-702 (2003)). Experimental mice received 0.2 ml of fresh inoculum by gastric gavage every other day for a total of three doses. Cecae and coli were collected at necropsy and analyzed by PCR using *H. hepaticus*-specific primers to confirm *Helicobacter* status.

Adoptive Transfer with Regulatory Lymphocytes

Adoptive transfer recipient mice were anesthetized with isofluorane and injected intravenously in the retro-orbital sinus with 3×10$^5$ cells suspended in 0.2 ml of HBSS. To obtain viable and highly purified cell populations, single cell suspensions of CD4$^+$CD45RB$^{lo}$CD25$^+$ lymphocytes from spleen and mesenteric lymph nodes from *Helicobacter*-free wildtype or IL10-deficient 129/SvEv donor mice were prepared as previously described (Erdman, et al., *Am. J. Pathol.* 162:691-702 (2003)). Half of the donor mice were males and half were females. Re-analysis of these cells prior to transfer into mice indicated that they were >96% pure.

Histologic Evaluation

Formalin-fixed tissues were embedded in paraffin, cut at 5 μm, and stained with hematoxylin and eosin. Lesions were scored by two pathologists blinded to sample identity. Hyperplastic and inflammatory lesions were graded on a scale of 0 to 4 with ascending severity as previously described (Erdman, et al., *Am. J. Pathol.* 162:691-702 (2003); Berg, et al., *J. Clin. Invest.:*98:1010-1020 (1996)). Epithelial dysplasia and neoplasia were graded using a scale of 0 to 4 based on a recently described scheme (Erdman, et al., *Am. J. Pathol.* 162:691-702 (2003); Boivin, et al., *Gastroenterology* 124:762-777 (2003)). Non-parametric data is presented as median score and range (in parentheses) for each group.

Treatment with IL10-Ig Fusion Protein

To produce the IL10-Ig fusion protein, murine IL10 was fused to the IgG2a CH2-CH3 regions, mutated at the Fc receptor binding site, using a PCR cloning strategy and the chimeric gene was cloned into an adenoviral vector and infectious virus generated (Ad-IL-10-Ig) as previously described (Mihara, et al., *J. Clin. Invest.* 106:91-101 (2000)). To generate higher titer stocks for these studies, Adv-IL10Ig was grown in 293 cells and purified by ultracentrifugation through two cesium chloride gradients. *Helicobacter*-free 129/SvEv Rag2-deficient mice were infected intravenously with 10$^{11}$ particles (5×10$^9$ pfu) of virus. Serum was harvested 10 days after infection and the concentration of fusion protein within the serum was quantified using an IgG2a-specific ELISA. The concentration of fusion protein in the serum was approximately 2 mg/ml and the half-life of the protein in serum was >3 days. We determined that 150 ng/ml of IL-10Ig was comparable to 1 ng/ml of recombinant IL-10 in its ability to inhibit the production of IL-12 p40 and IP-10 by IL-10-deficient macrophages. Serum containing 10 μg of fusion protein was administered by intraperitoneal injection to mice with established invasive cancer, twice weekly for one week.

Determination of Serum IL6 by ELISA

To determine serum IL6 concentration in treated and untreated mice, a sandwich ELISA was performed using QUANTIKINE® mouse IL6 kit (R&D Systems, MN) as per manufacturer's instructions. The IL6 standard curve and sample concentrations were determined by measuring absorbance at 450 nm and after applying correction for plate background (Biotek Instruments Inc., VT).

Treatment with Anti-IL6 Antibody

To determine whether IL6 is required for increased epithelial oncogene (Pim-1) expression and colonic cancer, mice with established carcinoma (n=8) were treated with 500 μg of rat anti-mouse IL6 (clone MP5-20F3; eBiosciences) by intraperitoneal injection twice weekly for one week. Matched control mice (n=8) received the same concentration of rat IgG1 (eBiosciences).

Gene Expression Analysis

RNA from colonic epithelium was purified according to Whitehead et al. (*Gastroenterology* 117:858-865 (1999)) with minor modifications. Briefly, colons were removed and flushed with ice-cold 1×PBS. Colons were then opened length-wise and incubated in 3 mM EDTA, 0.05 mM DTT for 60 minutes on ice at 4° C. Following the 1 hour incubation, tissues were rinsed once in cold 1×PBS. New PBS was added and the tissue was shaken vigorously to dislodge epithelium. The samples were then centrifuged to pellet the epithelium. Supernatant was removed and replaced with 1 ml of TRIZOL® (phenol/guanidine isothiocyanate) (Invitrogen). RNA was isolated according to manufacturer's instructions. After TRIZOL®, the RNA was further purified using Qiagen's RNeasy® (anion exchange column) Kit. Colonic epithelial cDNA was produced from 1 ug of purified RNA using SUPERSCRIPT III® reverse transcriptase (Invitrogen). For each treatment group, RNA was obtained from colons of at least 3 different animals. Gene expression analysis was performed by TaqMan® (PCR) analysis (Applied Biosystems, Foster City, Calif.) on an ABI Prism 7000 Sequence Detection System. All expression assays were designed by ABI (Assays-on-Demand™).

For each gene, the expression level relative to TATA box binding protein (Tbp) was assessed for at least 3 mice of each treatment group. The reactions were done in quadruplicate. For the control group, Rag2$^{-/-}$, the average expression level relative to Tbp was determined. Then, for each of the treatment groups, each single reaction was compared to the average of the control to generate a mean relative expression level for that group.

Statistical Analyses

Analyses of colonic lesion scores were performed using a Mann-Whitney U nonparametric test for ordinal data. Comparisons of frequency of carcinoma between groups were performed using a two-sided Fisher exact test. Statistical analysis of gene expression data was performed by Wilcoxon Rank Sum test using the Mstat computer program (mcardle.oncology.wisc.edu/mstat/).

B. Results and Discussion

Infection with *H. hepaticus* Induces Carcinoma

It has previously been demonstrated that *H. hepaticus* triggers colitis-associated cancer in Rag2$^{-/-}$ mice (Erdman, et al., *Am. J. Pathol.* 162:691-702 (2003); Erdman, et al., *Cancer Res.* 63:6042-6050 (2003)). The invasive neoplastic phenotype was exacerbated by prior adoptive transfer of IL10-deficient CD4$^+$CD45RB$^{lo}$CD25$^+$ lymphocytes. To determine whether *H. hepaticus* infection is required for carcinoma in this adoptive transfer model, we compared cell recipients challenged with *H. hepaticus* versus matched uninfected mice. While there were minimal changes in epithelial morphology in uninfected Rag2$^{-/-}$ mice treated with IL10$^{-/-}$ cells (n=10), significant changes including carcinoma were evident in animals with *H. hepaticus* infection (n=12). These data support the concept that microbial challenge coupled with incompetent regulatory lymphocytes contributes to tumorigenesis.

Treatment of Mice with IL10-Competent Regulatory Cells

Although we demonstrated previously that adoptive transfer with IL10-competent regulatory cells could abrogate colitis in *H. hepaticus*-infected Rag2$^{-/-}$ mice, it is unknown whether transfer of competent cells can rescue recipients of IL10$^{-/-}$ lymphocytes that have established carcinoma. To determine this, mice with established colon cancer underwent subsequent adoptive transfer with IL10-competent regulatory cells. When examined at one week after treatment, mice with tumors that received regulatory cells (n=10) had significantly less colitis (P<0.01) and cancer (P<0.001) than untreated controls (n=12). Treated mice examined up to 18 months after receipt of IL10-competent regulatory cells still had minimal lesions in the lower bowel.

Treatment of Mice with IL10-Ig

Since it was previously shown that regulatory lymphocytes require IL10 to inhibit microbially-induced carcinogenesis, we examined whether IL10 was sufficient to reverse malignancy and restore epithelial homeostasis in this model. To test this, mice with established colonic carcinoma were dosed twice weekly intraperitoneally with recombinant IL10-IgG2a fusion protein (IL10-Ig). A similar fusion protein was previously shown to exhibit IL10-like activity in vitro and in vivo (Zheng, et al., *J. Immunol.* 154:5590 (1995)). Colonic tissues were then examined at one week after onset of treatment. Recipients of IL10-Ig fusion protein (n=10) had minimal colitis (P<0.01) and no invasive cancer. Similar results are achieved using purified IL10-Fc in *H. hepaticus*-infected Rag2$^{-/-}$ mice. The finding that IL10-Ig fusion protein is sufficient to restore epithelial morphology identifies a key cytokine mediator of ongoing epithelial homeostasis in the bowel.

Expression of Tgfβ Pathway Genes

Given the phenotypic similarity of our mice and *H. hepaticus*-infected Tgfβ1-knockout mice (Engle, et al., *Cancer Res.* 62:6362-6366 (2002); Engle, et al., *Cancer Res.* 59:3379-3386 (1999)), we sought to determine whether Tgfβ signaling was disrupted in our model. We analyzed the gene expression of Tgfβ pathway members in *H. hepaticus*-infected Rag2$^{-/-}$ recipients of IL10$^{-/-}$ cells using quantitative RT-PCR (TaqMan). We found that Tgfβ1 gene was significantly overexpressed in purified colonic epithelium of mice at 6 weeks after infection with *Helicobacter*. Treatment with IL10-Ig led to normalized expression of Tgfβ1. We also analyzed the expression of TgfβRI, TgfβRII, and Smad4 gene. The expression of TgfβRI was not significantly affected by infection with *H. hepaticus*. By contrast, the expression of TgfβRII and Smad4 were increased in mice infected with *H. hepaticus*. We hypothesized that the over-expression of Tgfβ1, TgfβRII and Smad4 may be compensatory for a defect elsewhere in the signaling pathway (see below). This hypothesis is consistent with the finding that TgfβRII and Smad4 genes are also overexpressed in Tgfβ1-knockout mice.

Overexpression of IL6 and Pim-1

We next examined the expression of oncogenes known to be downstream of Tgfβ1 in epithelial cells (Kang, et al., *Mol. Cell.* 11:915-26 (2003)). Purified colonic epithelia from infected mice showed a significant increase in the expression of the Pim-1 and Bcl3 genes, but not c-Myc. The expression of Bcl3 was only slightly elevated in infected mice when compared with Pim. Overexpression of Pim-1 gene was intriguing given its role in prostate cancer (Kim, et al., *Oncogene* 23:1838-44 (2004)) and our finding that *H. hepaticus* infection promotes colon cancer predominantly in male mice (Erdman, et al., *Cancer Res.* 63:6042-6050 (2003)).

Based on these observations, we next tested expression of interleukin-6 (IL6), a cytokine known to regulate Pim-1 expression (Kim, et al., *Oncogene* 23:1838-44 (2004)), and found that IL-6 gene expression was increased in colonic epithelia of infected animals. In addition, IL-6 protein was elevated (μ=61.4 pg/ml) in sera of *H. hepaticus*-infected mice with colitis and cancer, but not in *Helicobacter*-free mice (μ=4.28 pg/ml). Changes in Pim-1 and IL6 gene expression were evident throughout the entire colonic epithelium and were not restricted to the multifocal invasive carcinomas, indicating generalized upregulation of cytokine and oncogene expression rather than focal genetic or epigenetic change.

We postulated that over-expression of oncogenes may also contribute to the colonic neoplasia in *H. hepaticus*-infected Tgfβ1 deficient mice. We found that the c-Myc, Bcl3, and Pim-1 genes were all significantly upregulated in the colonic epithelium of Tgfβ1$^{-/-}$ Rag2$^{-/-}$ mice. The finding that c-Myc is not overexpressed in *H. hepaticus*-infected Rag2$^{-/-}$ mice with carcinoma suggests that this gene does not play a central role in mediating the neoplastic phenotype in this model. We found also that IL6 was significantly overexpressed in *H. hepaticus*-infected Rag2$^{-/-}$ mice with germline mutation in Tgfβ1.

Recipients of IL10-Ig fusion protein sera demonstrated recovery of both IL6 and Pim-1 gene expression within colonic epithelia. Likewise, elevated serum IL6 returned to near baseline following treatment with IL10-Ig (μ=11 pg/ml). We hypothesized that the upregulation of IL6 resulting in overexpression of oncogenes, i.e., the Pim-1 gene, is responsible for the cancer phenotype in *Helicobacter*-infected animals. This hypothesis predicts that systemic treatment with anti-IL6, like treatment with IL10-Ig, will result in restoration of homeostasis and normalization of Pim-1 gene expression.

Treatment of Mice with Anti-IL6

Treatment with anti-IL6 antibody alone significantly (p<0.01) downregulated Pim-1 gene expression in colonic epithelia, commensurate with regression of mucinous carcinoma in *H. hepaticus*-infected Rag2$^{-/-}$ recipients of IL10-deficient cells. These observations indicate that IL10 is sufficient to modulate the colonic phenotype at the molecular and histological levels, likely through down-regulation of IL6. Indeed, IL10 has previously been shown to down-regulate IL6 in colitis in humans and mice (Powrie, et al, *Science* 299:1030-1031 (2003); Moore, et al., *Annu. Rev. Immunol.* 19:683-765 (2001)). These analyses demonstrate an association between microbially-induced colitis, invasive neoplastic epithelia, and overexpression of IL6 in colonic epithelia.

The elevated gene expression level of Pim-1 correlates with the histologic status of the colonic epithelium in our model. Cytokine-mediated normalization of epithelial Pim-1 expression coincident with tumor regression supports published reports that sustained oncogene expression is required for tumor maintenance. Indeed, Chin et al. (*Nature* 400:468-472 (1999)) demonstrated previously that sustained expression of oncogenic H-ras is required to maintain melanoma growth in transgenic mice.

Our studies are consistent with recent reports concerning 1) the relationship between oncogenes and inflammation-induced cancer and 2) the role of oncogene expression in tumor maintenance. We have found that the Pim-1 gene expression is upregulated in colons of mice infected with *H. hepaticus*. It is probable that this phenotype resulted from insufficiently down-regulated host inflammatory response, i.e., IL6, rather than bacteria counts per se. Earlier data showed that *H. hepaticus* counts are not significantly different between untreated mice and recipients of either IL10-deficient or competent regulatory cells Erdman, et al., *Cancer Res.* 63:6042-6050 (2003)). Although *H. hepaticus* was required to induce colonic carcinoma in these mouse models, it is likely that other enteric microbiota can also trigger carcinoma in genetically susceptible animals. Data from a mouse model of gastric cancer indicate that the overexpression of oncogenes can lower the threshold for microbially-induced cancer; in wild-type mice *H. felis* can be used to induce gastric cancer, yet mice overexpressing Cox2 and Pges1 in the glandular stomach develop gastric cancer in response to endogenous gut flora (Oshima, et al., *Embo J* 23:1669-78 (2004)). Based on this observation, we would predict that overexpression of the IL6 or Pim-1 genes in the colonic epithelium may lead to carcinoma in the presence of endogenous microbial flora alone.

All references cited herein are fully incorporated by reference in their entirety. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of treating a patient for an adenocarcinoma of the colon which does not occur subsequent to an inflammatory bowel disease and which overexpresses the Pim-1 oncogene, comprising administering to said patient an effective amount of a chimeric protein in which human IL10 is fused to the Fc region of a human IgG and wherein said chimeric protein has a circulating plasma half-life that is at least twice as long as free human IL10.

2. The method of claim 1, wherein said human IgG is human IgG2a.

3. The method of claim 1, wherein said chimeric protein further comprises the hinge region of IgG and said IL10 is fused to said hinge region.

4. The method of claim 1, wherein said chimeric protein has a circulating plasma half-life of at least four hours.

5. The method of claim 1, wherein said chimeric protein is administered to said patient by injection or infusion at a dose of 0.5 µg/kg body weight to 50 µg/kg body weight.

6. The method of claim 1, wherein said Fc region of said human IgG is non-lytic.

7. The method of claim 1, wherein said chimeric protein is administered to said patient by injection or infusion at a dose of 0.5-5 mg.

8. The method of claim 1, wherein:
   a) said human IgG is human IgG2a;
   b) said chimeric protein further comprises the hinge region of IgG and said IL10 is fused to said hinge region; and
   c) said chimeric protein has a circulating plasma half-life of at least four hours.

9. The method of claim 8, wherein said Fc region of said human IgG is non-lytic.

10. The method of claim 9, wherein said chimeric protein is administered to said patient by injection or infusion at a dose of 0.5-5 mg.

11. A method of treating a patient for an adenocarcinoma of the colon which does not occur subsequent to an inflammatory bowel disease, comprising:
   a) assaying a biological sample from said patient to determine if said adenocarcinoma is producing more Pim-1 oncogene than the amount produced by normal tissue of the same organ; and

SEQUENCE LISTING

<160> NUMBER OF SEQ ID NOS: 2

<210> SEQ ID NO 1
<211> LENGTH: 43
<212> TYPE: DNA
<213> ORGANISM: Mus musculus

<400> SEQUENCE: 1
acatgacaat taaagccagg ctggagccca gagggcccac aat          43

<210> SEQ ID NO 2
<211> LENGTH: 23
<212> TYPE: DNA
<213> ORGANISM: Mus musculus

<400> SEQUENCE: 2
tttctagatc atttacccgg agt          23 b) if the results of the assay of step a) indicate that said adenocarcinoma is producing greater than normal amounts of said Pim-1 oncogene, administering to said patient a pharmaceutical composition comprising an effective amount of a chimeric protein in which human IL10 is fused to the Fc region of a human IgG and wherein said chimeric protein has a circulating plasma half-life that is at least twice as long as free human IL10.

12. The method of claim 11, wherein said chimeric protein has a circulating plasma half-life of at least four hours.

13. The method of claim 12, wherein said chimeric protein is administered at a dosage of between 0.5 µg/kg body weight and 50 µg/kg body weight.

14. The method of claim 11, wherein said human IgG is human IgG2a.

15. The method of claim 14, wherein said chimeric protein further comprises the hinge region of IgG and said IL10 is fused to said hinge region.

16. The method of claim 15, wherein said Fc region of said human IgG is non-lytic.

17. The method of claim 16, wherein said chimeric protein has a circulating plasma half-life of at least four hours.

18. The method of claim 17, wherein said chimeric protein is administered to said patient by injection or infusion at a dose of 0.5 µg/kg body weight to 50 µg/kg body weight.

19. The method of claim 18, wherein said chimeric protein is administered to said patient by injection or infusion at a dose of 0.5-5 mg.

20. The method of claim 18, wherein the assay of step a) is an ELISA assay.

* * * * *